United States Patent [19]

Matthews et al.

[11] 4,263,320

[45] Apr. 21, 1981

[54] HYPOGLYCEMIC PHENYLPROPYNYLAMINO BENZOIC ACIDS

[75] Inventors: Donald P. Matthews, Indianapolis; Eugene R. Wagner, Carmel; Roger D. McDermott, Noblesville, all of Ind.

[73] Assignee: The Dow Chemical Company, Midland, Mich.

[21] Appl. No.: 44,877

[22] Filed: Jun. 4, 1979

[51] Int. Cl.³ .................... C07A 101/52; A01N 37/12
[52] U.S. Cl. .................................. 424/319; 562/456; 562/457
[58] Field of Search ................ 562/457, 456; 560/48; 424/309, 319

[56] References Cited

U.S. PATENT DOCUMENTS

| | | | |
|---|---|---|---|
| 3,657,430 | 4/1972 | Shen et al. | 424/309 |
| 3,868,416 | 2/1975 | Albright et al. | 560/19 |
| 3,957,850 | 5/1976 | Bouchara | 560/19 |
| 3,983,164 | 9/1976 | Thorne | 562/433 |

FOREIGN PATENT DOCUMENTS 7602332  9/1976  Netherlands ............... 560/19

Primary Examiner—James H. Reamer
Attorney, Agent, or Firm—G. D. Street

[57] ABSTRACT

Hypoglycemic phenylpropynylamino benzoic acids and the pharmaceutically-acceptable salts thereof, a method for lowering serum sugars and hypoglycemic compositions useful for the treatment of diabetes.

19 Claims, No Drawings

HYPOGLYCEMIC PHENYLPROPYNYLAMINO BENZOIC ACIDS

CROSS-REFERENCE TO RELATED APPLICATION

This is a continuation of application Ser. No. 918,547, filed June 23, 1978, now abandoned.

BACKGROUND OF THE INVENTION

Diabetes mellitus is a disease of mammals which is characterized by an intolerance to carbohydrates and an inadequate production and secretion of insulin by the $\beta$-cells in the islets of Langerhans. The disease is often associated with vascular degeneration, especially atherosclerosis. Hypoglycemic agents which are effective in lowering blood sugars may be used in the treatment of certain types of diabetes. U.S. Pat. No. 3,983,164 describes a group of benzoic acid derivatives which have demonstrated hypoglycemic activity.

SUMMARY OF THE INVENTION

The present invention relates to novel phenylpropynylaminobenzoic acid compounds and the pharmaceutically-acceptable salts thereof which have been found to be active as hypoglycemic agents. The present invention also relates to a method of use of these compounds in lowering blood sugar in a mammal and to hypoglycemic compositions comprising the active compound in combination with a pharmaceutically-acceptable carrier and other excipients.

Compounds falling within the scope of the present invention may be represented by the general formula

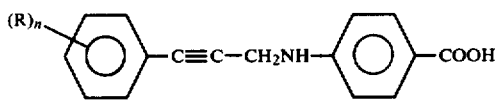

wherein R independently and at each occurrence represents halo, alkyl or alkoxy and n represents the integer 0, 1, or 2. As used herein the terms "alkyl" and "alkoxy" refer to a moiety having from one to about three carbon atoms in a chain either branched or unbranched. The term halo refers to a halogen substitution on the phenyl ring selected from the group consisting of fluoro, chloro, bromo, and iodo, with fluoro and chloro being preferred.

Pharmaceutically-acceptable salts of the phenylpropynylaminobenzoic acid compounds described herein are considered as being within the scope of the invention. Pharmaceutically-acceptable salts refer to the acid addition salts of those bases which will form a salt with the carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydrooxide, calcium hydroxide, potassium carbonate, sodium bicarbonate, magnesium carbonate and the like, ammonia, primary, secondary, and tertiary amines and the like. Also aluminum salts of the instant compounds may be obtained by treating the corresponding sodium salt with an appropriate aluminum complex such as, for example, aluminum chloride hexahydrate, and the like.

The phenylpropynylaminobenzoic acids described above and their pharmaceutically-acceptable salts when used according to the method of the present invention show hypoglycemic activity in mammals, i.e. lower the level of sugar in the blood. The compounds of the present invention are therefore particularly suitable for use in the treatment of diabetes in mammals characterized by abnormally high levels of glucose in the blood. The compounds can be administered internally to the mammal either orally or parenterally by subcutaneous, intravenous, or intraperitoneal injection or by implantation or the like. Oral administration is generally preferred.

The effective hypoglycemic amount of the active compounds to be internally administered to a mammal, that is the amount which is effective to significantly lower the amount of sugar in the blood, can vary depending upon such factors as the particular phenylpropynylaminobenzoic acid or pharmaceutically-acceptable salt employed, the desired level of blood sugar to be obtained, the severity of the disease, the period of administration, and the method of administration. In general, an effective daily dosage range is from about 15 to about 180 milligrams per kilogram of body weight, with a daily dosage range of from about 15 to about 60 milligrams per kilograms of body weight being preferred.

DETAILED DESCRIPTION OF THE INVENTION

The compounds of the present invention are prepared by condensing a pre-selected phenylpropargyl aldehyde with p-aminobenzoic acid. The resulting Schiff base is reduced to prepare the corresponding free acid. A convenient method of carrying out the latter procedure involves mixing about 0.1 mol. of the Schiff base with an excess of ethanol and water. Dilute aqueous sodium hydroxide, for example, in an amount of about 0.1 molar equivalent of the Schiff base optionally can be added to the mixture. Sodium borohydride (0.1 ml) is added at about room temperature and stirred until it dissolves. Other suitable reducing agents, such as for example dimethylamino borane, may also be used to reduce the Schiff base to the free acid. The mixture is heated at reflux for about 1 or 2 hours. The product may be separated from the mixture by known procedures and further purified if desired.

The phenylprogargyl aldehydes used as a starting material were prepared from a pre-selected acetal by treatment with acetonitrile and p-toluenesulfonic acid. The acetal may be prepared from a derivative of benzaldehyde using the method described by Corey and Fuchs, *Tetrehedron Letters*, pages 3769–3772 (1972).

Pharmaceutically-acceptable salts of the acid may be prepared by treating the free acid with an appropriate base, that is a base which will form a pharmaceutically-acceptable salt with the carboxylic acid and the anions of which are relatively innocuous at dosages consistent with good pharmacological activity so that the desired hypoglycemic properties of the salt are not vitiated by side effects ascribable to the anions.

In carrying out the method of the present invention, the active compound can be administered directly or as an active ingredient of a pharmaceutical preparation or composition. To illustrate, for oral administration, pharmaceutical preparations of the phenylpropynylamino benzoic acids may be made by following the conventional techniques of the pharmaceutical chemist. These techniques involve granulating and compressing the active compound alone or in admixture with other materials or variously mixing and dissolving or suspending the active compound with other ingredients as appropriate to prepare a predetermined end product. Numerous pharmaceutical forms to carry the compound can be used. For example, the pure compound can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions make take the form of tablets, linguets, powders, capsules, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate, disintegrating agents such as maize starch or alginic acid, and lubricating agents such as magnesium stearate may be used.

If a liquid carrier is used, the preparation may be in the form of a soft gelatin capsule, a syrup, a liquid solution or a suspension.

The hydrocarbon solubility of the compounds of this invention generally is sufficiently high to allow the use of pharmaceutically-acceptable oils either as a solvent or as a carrier. For example vegetable or animal oils such as sunflower oil, safflower oil, maize oil or cod liver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

The phenylpropynylamino benzoic acids or salt used in the method of the present invention also can be incorporated in a nutritive foodstuff such as, for example, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Expecially satisfactory are the pharmaceutically acceptable glycols, such as propylene glycol, and mixtures thereof. Glycerine is another example of a polyol which is particularly useful. Up to 25-30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

The following examples will serve to further clarify the present invention, but are not to be construed as a limitation thereon.

EXAMPLE 1

Preparation of 4-((3-phenyl-2-propynyl)-amino) benzoic acid

A mixture containing 19.5 grams (0.15 moles) of phenylpropargyl aldehyde, 20.6 grams (0.15 moles) pf p-aminobenzoic acid, 400 ml. of benzene, and 0.1 grams of p-toluenesulfonic acid was heated to reflux, while water that formed was collected in a Dean-Stark trap. The reaction was allowed to proceed for about one hour, after which period the reaction mass was cooled, and the imine was collected.

After drying the resulting imine was reduced by mixing 29.2 grams (0.117 moles) with 25 ml. of 5 Normal sodium hydroxide, 50 ml. of water, 400 ml. of ethanol, and 4.5 grams (0.12 moles) of sodium borohydride. The mixture was allowed to reflux for about two hours, after which period the reaction mass was mixed with ice water and acidified with concentrated hydrochloric acid. The product was collected as a light yellow solid and dried. The crude material was recrystallized from acetonitrile to give 17.9 grams (60% yield) of a light yellow powder. The 4-((3-phenyl-2-propynyl)amino)-benzoic acid was found to have a melting point of 164°-166° C.

Elemental analysis found carbon 76.2%, hydrogen 5.25%, and nitrogen 5.62% as compared to theoretical values of carbon 76.5%, hydrogen 5.21%, and nitrogen, 5.57%.

EXAMPLE 2

Preparation of 4-((3-phenyl-2-propynyl)-amino)benzoic acid-sodium salt

A mixture of 10.0 grams (0.04 moles) of 4-((3-phenyl-2-propynyl)amino)benzoic acid and 100 ml. of acetone was brought to reflux and 3.2 ml. of 50% sodium hydroxide (0.04 moles) was added dropwise. Water was added slowly (about 8 ml) until solution was achieved. The mixture was filtered and cooled. Crystallization of the product was induced by the addition of a few seed crystals. The sodium salt was collected and washed with acetone. The light yellow title compound was recrystallized from a mixture of acetone and water (100 ml acetone/5 ml water). The salt was found to have a melting point in excess of 250° C.

EXAMPLE 3
Preparation of 4-((3-(4-fluoro)phenyl-2-propynyl)amino)benzoic acid A mixture containing 13.4 grams (0.06 moles) of 4-fluorophenylpropargyl aldehyde diethyl acetal, 50 ml. of acetonitrile, 10 ml. of water, and 1 gram of p-toluenesulfonic acid was warmed at 50° C. for about one hour. The reaction was mixed with about 200 ml. of water and 200 ml. of methylene chloride. The methylene chloride layer was dried with sodium sulfate and concentrated to yield the 4-fluorophenylpropargyl aldehyde intermediate as a pale yellow oil which rapidly crystallized.

The 4-fluorophenylpropargyl aldehyde thus formed was subsequently used to prepare 4-((3-(4-fluoro)-phenyl-2-propynyl)amino)benzoic acid using methods already described above. The melting point was found to be 216°–218° C.

Using methods already described above the following compounds were also prepared.

EXAMPLE 4
4-((3-(4-Chloro)phenyl-2-propynyl)amino)-benzoic acid, melting point 215°–218° C.

EXAMPLE 5
4-((3-(4-Methyl)phenyl-2-propynyl)amino)-benzoic acid, melting point 214°–216° C.

The hypoglycemic activity of the subject compounds may be demonstrated in alanine-induced hyperglycemic mice. Alanine is the most glucogenic of the amino acids and also stimulates gluconeogensis in normal animals. Animals suffering from diabetes show an exaggerated hyperglycemic response to a protein or amino acid meal, therefore the hyperglycemic state induced by alanine closely parallels the response of a diabetic mammal.

The studies were carried out by interperitoneally injecting fasted male Swiss-Webster mice with various pre-determined doses of the active compound. Fifteen minutes later the same mice were injected intrapertioneally with 10 m moles/kg body weight of L-alanine. Sixty minutes after injection of the active compound, the animals were sacrificed and their sera were analyzed for glucose. The control consisted of both fasted mice and mice injected with alanine only. The results are expressed as percent lowering of serum glucose from the alanine-induced hyperglycemic level to the fasted control glucose level, i.e. lowering to the fasting glucose level is 100% lowering. The results are shown in Table I.

TABLE I

| Compound Example Number | Dosage Level (mg/kg.)* | | | | |
|---|---|---|---|---|---|
| | 7.5 | 15 | 30 | 60 | ED$_{50}$** |
| 1 | 36 | 79 | 98 | 132 | 8 |
| 2 | 44 | 69 | 114 | 139 | — |
| 3 | 2 | 66 | 91 | 172 | 18 |
| 4 | — | — | — | 39 | — |
| 5 | 9 | 15 | 118 | 76 | 21 |

*data expressed as percent lowering of serum glucose as compared to controls.
**effective dose The results demonstrate the hypoglycemic activity of representative compounds falling within the scope of the present invention. The most active compounds and the preferred embodiments of the invention are 4-((3-phenyl-2-propynyl)amino)benzoic acid (Example 1) and its sodium salt (Example 2). The other compounds falling within the scope of the present invention while less active as hypoglycemic agents also showed satisfactory activity in lowering the amount of glucose in the serum of the test animals. The data also demonstrates there is no significant difference in activity between the free acid and its pharmaceutically-acceptable salts.

We claim:

1. A compound having the formula

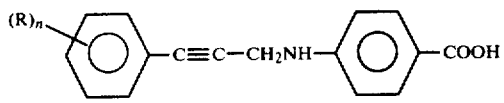

wherein R independently and at each occurrence represents halo, alkyl or alkoxy and n represents the integer 0, 1, or 2 and further including the pharmaceutically-acceptable salts thereof.

2. The compound of claim 1 which is 4-((3-phenyl-2-propynyl)amino)benzoic acid or a pharmaceutically-acceptable salt thereof.

3. The compound of claim 2 which is 4-((-3-phenyl-2-propynyl)amino)benzoic acid-sodium salt.

4. The compound of claim 1 which is 4-((3-(4-fluoro)phenyl-2-propynyl)amino)benzoic acid and the pharmaceutically-acceptable salts thereof.

5. The compound of claim 1 which is 4-((3-(4-chloro)-phenyl-2-propynyl)amino)benzoic acid and the pharmaceutically-acceptable salts thereof.

6. The compound of claim 1 which is 4-((3--(4-methyl)phenyl-2-propynyl) amino) benzoic acid and the pharmaceutically-acceptable salts thereof.

7. A method for treating hyperglycemia in a mammal which comprises administering internally to the mammal an effective hypoglycemic amount of a compound or pharmaceutically-acceptable salt thereof having the formula

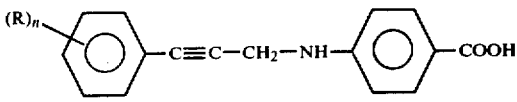

wherein R independently and at each occurrence represents halo, alkyl or alkoxy and n represents the integer 0, 1, or 2.

8. The method of claim 7 wherein the compound is 4-((3-phenyl-2-propynyl)amino)benzoic acid or a pharmaceutically-acceptable salt thereof.

9. The method of claim 8 wherein the compound is the sodium salt.

10. The method of claim 7 wherein the compound is 4-((3-(4-fluoro)phenyl-2-propynyl)amino)benzoic acid and the pharmaceutically-acceptable salts thereof.

11. The method of claim 7 wherein the compound is 4-((3-(4-chloro)phenyl-2-propynyl)amino)benzoic acid or a pharmaceutically-acceptable salt thereof.

12. The method of claim 7 wherein the compound is 4-((3-(4-methyl)phenyl-2-propynyl)amino)benzoic acid or a pharmaceutically-acceptable salt thereof.

13. The method of claim 7 wherein the mammal is diabetic.

14. A composition for the treatment of hyperglycemia in a mammal which comprises a pharmaceutically-acceptable carrier in combination with a hypoglycemic amount of a compound or a pharmaceutically-acceptable salt thereof having the formula

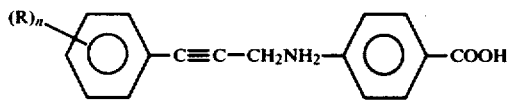

wherein R independently and at each occurrence represents halo, alkyl or alkoxy and n represents the integer 0, 1, or 2.

15. The composition of claim 14 wherein the compound is 4-((3-phenyl-2-propynyl)amino)benzoic acid or a pharmaceutically-acceptable salt thereof.

16. The composition of claim 15 wherein the compound is the sodium salt.

17. The composition of claim 14 wherein the compound is 4-((3-(4-fluoro)phenyl-2-propynyl)amino)-benzoic acid or a pharmaceutically-acceptable salt thereof.

18. The composition of claim 14 wherein the compound is 4-((3-(4-chloro)phenyl-2-propynyl)amino)-benzoic acid or a pharmaceutically-acceptable salt thereof.

19. The composition of claim 14 wherein the compound is 4-((3-(4-methyl)phenyl-2-propynyl)amino)-benzoic acid or a pharmaceutically-acceptable salt thereof.

* * * * *